US012053584B1

(12) United States Patent
Truong et al.

(10) Patent No.: US 12,053,584 B1
(45) Date of Patent: Aug. 6, 2024

(54) COUPLER

(71) Applicant: Telesair, Inc., Irvine, CA (US)

(72) Inventors: Hector Truong, Westminster, CA (US); Chi Wai Choy, Irvine, CA (US); Bo Li, San Diego, CA (US)

(73) Assignee: Telesair, Inc., Irvine, CA (US)

( * ) Notice: Subject to any disclaimer, the term of this patent is extended or adjusted under 35 U.S.C. 154(b) by 0 days.

(21) Appl. No.: 18/169,374

(22) Filed: Feb. 15, 2023

(51) Int. Cl.
| A61M 16/08 | (2006.01) |
| A61M 16/00 | (2006.01) |
| A61M 16/10 | (2006.01) |
| A61M 16/20 | (2006.01) |

(52) U.S. Cl.
CPC ...... *A61M 16/0841* (2014.02); *A61M 16/024* (2017.08); *A61M 16/0816* (2013.01); *A61M 16/085* (2014.02); *A61M 16/0866* (2014.02); *A61M 16/0875* (2013.01); *A61M 16/1005* (2014.02); *A61M 16/1095* (2014.02); *A61M 2016/102* (2013.01); *A61M 2016/1025* (2013.01); *A61M 16/107* (2014.02); *A61M 16/208* (2013.01); *A61M 2205/3368* (2013.01);
(Continued)

(58) Field of Classification Search
CPC ............ A61M 16/0057; A61M 16/022; A61M 16/024; A61M 16/08; A61M 16/0816; A61M 16/0833; A61M 16/0841; A61M 16/085; A61M 16/0866; A61M 16/0875; A61M 16/1005; A61M 16/107; A61M 16/1095; A61M 16/161; A61M 16/208; A61M 2016/102; A61M 2016/1025; A61M 2230/205; A61M 2205/3368; A61M 2205/7509

See application file for complete search history.

(56) References Cited

U.S. PATENT DOCUMENTS

| 4,686,354 | A | | 8/1987 | Makin |
| 5,392,770 | A | * | 2/1995 | Clawson ............ A61M 16/1095 128/912 |
| 5,676,132 | A | | 10/1997 | Tillotson et al. |
| (Continued) | | | | |

FOREIGN PATENT DOCUMENTS

| EP | 3766534 A1 | 1/2021 | |
| WO | WO-2021069550 A1 | * 4/2021 | ........ A61M 16/0816 |
| WO | WO-2022203523 A1 | * 9/2022 | ............ A61M 16/16 |

OTHER PUBLICATIONS

Machine translation of WO-2021069550-A1.*
(Continued)

*Primary Examiner* — Joseph D. Boecker
(74) *Attorney, Agent, or Firm* — Maier & Maier, PLLC

(57) ABSTRACT

A coupler includes: a first connecting portion, an accommodating portion, and a second connecting portion; the first connecting portion is operatively connected to a gas-providing circuit; the second connecting portion is operatively connected to a gas-delivering circuit, where the gas-providing circuit, the coupler and the gas-delivering circuit form a pathway for providing gas to a user at a patient side of the coupler; the accommodating portion is provided with at least one sensing apparatus or a heating apparatus, where the at least one sensing apparatus is configured to measure a first parameter of the gas, and the heating apparatus is configured to heat the gas passing through the coupler.

17 Claims, 2 Drawing Sheets

(52) U.S. Cl.
CPC .............. *A61M 2205/7509* (2013.01); *A61M 2230/205* (2013.01); *A61M 2230/42* (2013.01)

(56) References Cited

U.S. PATENT DOCUMENTS

| | | | |
|---|---|---|---|
| 8,453,641 B2 | 6/2013 | Payton et al. | |
| 9,265,902 B2 | 2/2016 | Payton et al. | |
| 9,572,949 B2 | 2/2017 | Vos et al. | |
| 10,363,382 B2 | 7/2019 | Vos et al. | |
| 10,537,698 B2 | 1/2020 | Payton et al. | |
| 2004/0182392 A1* | 9/2004 | Gerder | A61M 16/08 128/204.22 |
| 2004/0187871 A1* | 9/2004 | Kimmel | A61B 5/4833 128/204.23 |
| 2010/0168599 A1* | 7/2010 | Esposito | A61M 16/0858 600/532 |
| 2012/0125333 A1* | 5/2012 | Bedford | A61M 16/109 128/205.12 |
| 2012/0232420 A1 | 9/2012 | Salamitou | |
| 2013/0253336 A1* | 9/2013 | Haveri | A61M 16/0816 600/476 |
| 2014/0311487 A1* | 10/2014 | Buechi | A61M 16/021 128/203.14 |
| 2015/0101600 A1* | 4/2015 | Miller | A61M 16/161 128/203.14 |
| 2016/0354573 A1* | 12/2016 | Buswell | A61M 16/1095 |
| 2017/0074695 A1* | 3/2017 | Baecke | G01L 19/0038 |
| 2017/0266399 A1* | 9/2017 | Campana | A61M 16/107 |
| 2018/0250481 A1 | 9/2018 | Salamitou et al. | |
| 2019/0275281 A1* | 9/2019 | Creusot | A61M 16/109 |
| 2020/0023156 A1 | 1/2020 | Miller et al. | |
| 2021/0046265 A1* | 2/2021 | Obenchain | A61M 16/0666 |
| 2021/0077765 A1* | 3/2021 | Peiris | A61M 16/1095 |

OTHER PUBLICATIONS

International Search Report and Written Opinion issued on Jun. 3, 2024, in corresponding International Application No. PCT/US2024/015183, 10 pages.

* cited by examiner

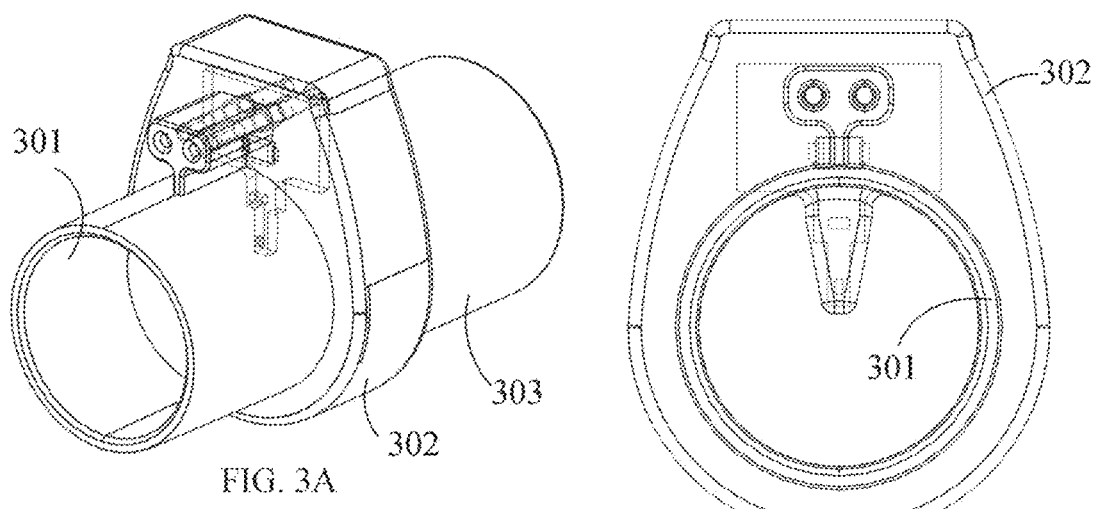
FIG. 3A
FIG. 3B
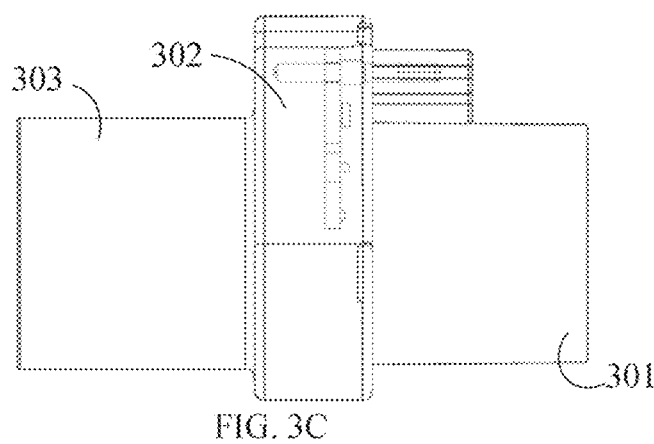
FIG. 3C
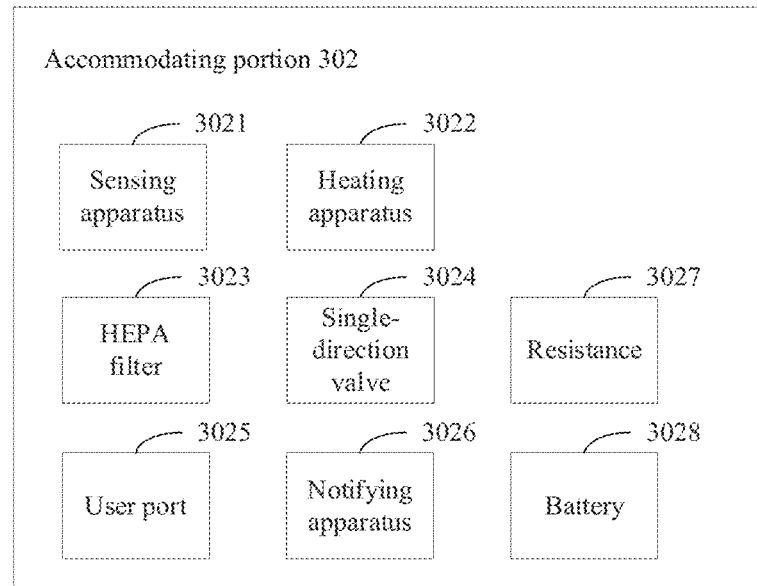
FIG. 4

COUPLER

TECHNICAL FIELD

The present application relates to the technical field of medical treatment, and in particular, to a coupler.

BACKGROUND

In recent years, a high flow oxygen therapy (HFOT) system has been developed to provide respiratory support for a patient who is unable to ensure enough ventilation by their own respiratory efforts, for example, a patient who suffers from a respiratory disease caused by the COVID-19 virus.

The HFOT system functions to assist the patient with respiratory insufficiency by exchanging gas and energy (such as thermal energy) with assistance of a breathing circuit with functions of heating and temperature sensing. Typically, oxygen, in conjunction with compressed air and humidification, is delivered to the patient through the HFOT system at a flow rate higher than that delivered in traditional oxygen therapy.

This background information is provided to reveal information believed by the applicant to be of possible relevance to the present application. No admission is necessarily intended, nor should be construed, that any of the preceding information constitutes prior art against the present application.

SUMMARY

Embodiments of the present application provide a coupler.

The foregoing and other objects are achieved by the subject matter of the independent claims. Further implementation forms are apparent from the dependent claims, the description and the figures.

A first aspect of the present application provides a coupler, including: a first connecting portion, an accommodating portion and a second connecting portion;
the first connecting portion is operatively connected to a gas-providing circuit;
the second connecting portion is operatively connected to a gas-delivering circuit, where the gas-providing circuit, the coupler and the gas-delivering circuit form a pathway for providing gas to a user at a patient side of the coupler;
the accommodating portion is provided with at least one sensing apparatus, where the at least one sensing apparatus is configured to measure a first parameter of the gas passing through the coupler.

In a possible implementation, the gas-providing circuit includes a main board device configured for providing the gas;
the coupler is communicatively connected to the main board device;
the at least one sensing apparatus is configured to send the first parameter of the gas to the main board device.

In a possible implementation, the coupler is powered by the main board device.

In a possible implementation, a working mode of the coupler is acquired by the main board device according to attribute information provided by the coupler.

In a possible implementation, the coupler further includes a resistance provided in the accommodating portion;

where the attribute information is a value of the resistance, and different values of the resistance correspond to different working modes of the coupler.

In a possible implementation, different working modes of the coupler correspond to different flow rates of the gas.

In a possible implementation, a coupling mode set on the main board device is adjusted by the main board device according to the working mode of the coupler.

In a possible implementation, the coupler further includes a notifying apparatus provided in the accommodating portion;
where the notifying apparatus is triggered to generate a notification under a condition that the working mode of the coupler is inconsistency with a coupling mode set on the gas provider.

In a possible implementation, the notifying apparatus is an audio speaker or a light emitting diode provided in the accommodating portion.

In a possible implementation, the coupler is triggered to operate upon receiving a triggering instruction from the main board device.

In a possible implementation, the gas-providing circuit further includes a gas-heating conduit;
the gas heating conduit is operatively connected to the main board device and the first connecting portion of the coupler respectively;
the gas-heating conduit is configured to heat the gas provided by the main board device.

In a possible implementation, the coupler is triggered to operate under a condition that the first connecting portion and the second connecting portion are respectively assembled to the gas-providing circuit and the gas-delivering circuit.

In a possible implementation, the coupler further includes a battery for providing power for the coupler.

In a possible implementation, the coupler further includes at least one of an HEPA filter or a single direction valve provided in the accommodating portion.

In a possible implementation, the coupler further includes a user port provided in the accommodating portion, where the user port is configured to collect physiological information of the user.

In a possible implementation, the coupler is operatively connected to the gas-providing circuit in a sealed manner.

In a possible implementation, the at least one sensing apparatus includes at least one of an FiO2 sensor, an SpO2 sensor, a humidity sensor, a sensor for detecting a breath rate, a sensor for detecting an ambient temperature, or a sensor for detecting a temperature of the gas.

In a possible implementation, the gas-delivering circuit is one of a nasal cannula, a tracheostomy tube, and a respiratory mask.

In a possible implementation, the coupler further includes a heating apparatus configured to heat the gas passing through the coupler.

In a possible implementation, at least one sensing apparatus or the heating apparatus is operatively connected to the accommodating portion in a detachable manner.

The present application provides a coupler. The coupler includes: a first connecting portion, an accommodating portion and a second connecting portion; the first connecting portion is operatively connected to a gas-providing circuit; the second connecting portion is operatively connected to a gas-delivering circuit, where the gas-providing circuit, the coupler and the gas-delivering circuit form a pathway for providing gas to a user at a patient side of the coupler; the accommodating portion is provided with at least one sensing apparatus or a heating apparatus, where the at least one sensing apparatus is configured to measure a first parameter of the gas passing through the coupler.

BRIEF DESCRIPTION OF DRAWINGS

The accompanying drawings are used to provide a further understanding of the present application, constitute a part of the specification, and are used to explain the present application together with the following specific embodiments, but should not be construed as limiting the present application.

FIG. 3A shows a schematic diagram of a coupler provided by an embodiment of the present application.

FIG. 3B shows a schematic diagram of a coupler provided by an embodiment of the present application.

FIG. 3C shows a schematic diagram of a coupler provided by an embodiment of the present application.

FIG. 4 shows a schematic block diagram of an accommodating portion of a coupler provided by an embodiment of the present application.

DETAILED DESCRIPTION OF THE EMBODIMENTS

In the following description, reference is made to the accompanying figures, which form part of the application, and which show, by way of illustration, specific aspects of embodiments of the present application or specific aspects in which embodiments of the present application may be used. It is understood that embodiments of the present application may be used in other aspects and include structural or logical changes not depicted in the figures. The following detailed description, therefore, is not to be taken in a limiting sense, and the scope of the present application is defined by the appended claims.

A respiratory system, such as a high flow oxygen therapy (HFOT) system is widely used in the field of medical treatment. For example, when a patient suffers from a respiratory disease caused by the COVID-19 virus, the patient generally has trouble in ensuring enough ventilation by his own respiratory efforts. In such a case, the HFOT system can be employed to provide respiratory support for the patient having respiratory insufficiency. Specifically, a breathing circuit is provided in the HFOT system and plays an important role in the operation of the HFOT system. The breathing circuit specifically serves to heat the gas flowing inside the HFOT system and detect temperature of the gas, so that the heated gas consisted of oxygen and compressed air is delivered to the patient so as to alleviate discomfort of the patient caused by the respiratory disease.

However, in the existing art, functions such as heating and temperature sensing are integrated into the breathing circuit in the exemplary HFOT system, which causes inflexibility as well as difficulty in expansion of additional functions of the HFOT system. Therefore, the present application provides a coupler to solve the above mentioned problems.

In the following, the technical solutions of the present application will be described in detail with reference to the accompanying drawings.

Figure 1:
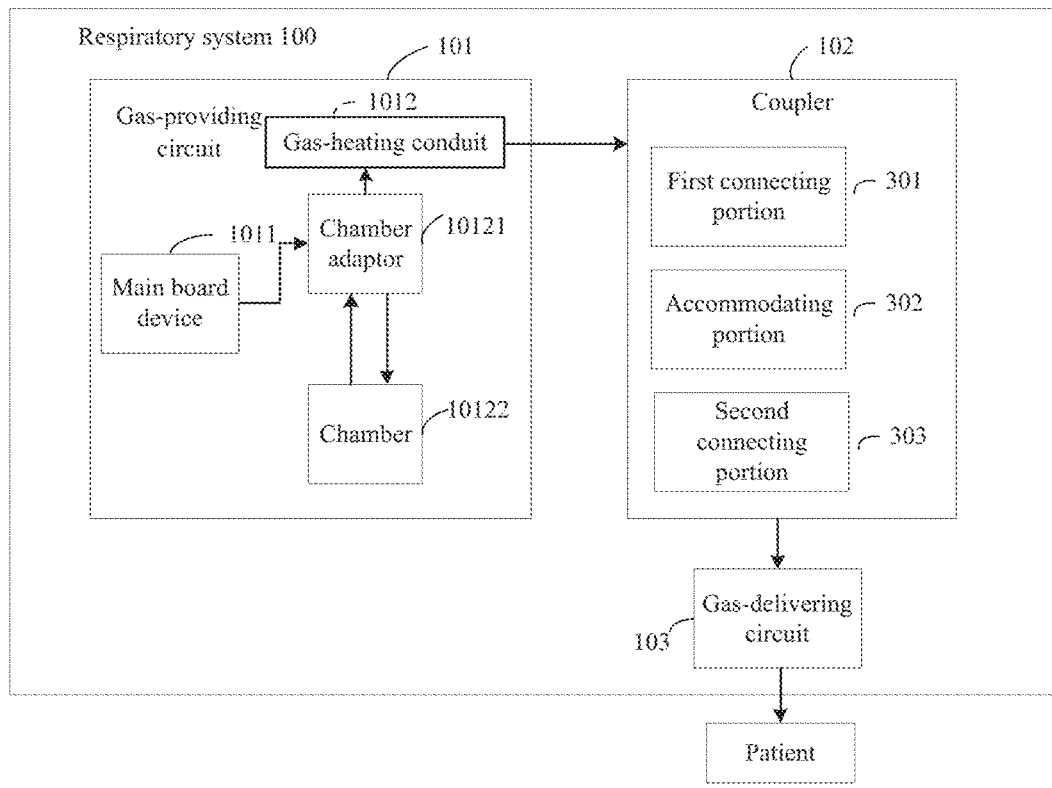
FIG. 1 shows a schematic block diagram of a respiratory system provided by an embodiment of the present application.

FIG. 1 shows a schematic block diagram of a respiratory system provided by an embodiment of the present application.

As shown in FIG. 1, the respiratory system 100 (e.g., the HFOT system) includes a gas-providing circuit 101, a coupler 102 and a gas-delivering circuit 103. In a possible implementation, the gas-providing circuit 101 includes a main board device 1011 configured for providing gas. The respiratory system 100 serves to deliver the gas, such as humidified and heated oxygen in conjunction with compressed air, to the patient at a flow rate which may be higher than that delivered in traditional oxygen therapy. It is to be noted that the arrows between different blocks in FIG. 1 represent a one-way flow path of the gas within the respiratory system.

In a possible implementation, the gas-providing circuit 101 may further include a gas-heating conduit 1012, where the gas-heating conduit 1012 may include a chamber adaptor 10121 and a chamber 10122 as shown in FIG. 1. The main board device 1011 is configured to provide oxygen and compressed air to the chamber adaptor 10121 for further processing. In a possible implementation, the main board device 1011 also serves to control the operating of the respiratory system 100, for example, the main board device 1011 can adjust operating parameters of the respiratory system 100, and process data fed back by other components of the respiratory system 100. Such heating may also be implemented through a heating apparatus (e.g., 3022 in FIG. 4) provided in the coupler, which will be elaborated later.

The chamber adaptor 10121 is configured to direct the gas to flow along a predefined pathway inside the respiratory system 100. Specifically, the gas flowing inside the respiratory system 100 is directed from the main board device 1011 to the chamber 10122 through the chamber adaptor 10121 first, and then the gas is directed from the chamber 10122 to the coupler 102 through the chamber adaptor 10121, where the chamber 10122 is configured to store liquid for humidifying the gas flowing through the chamber 10122. Subsequently, the gas is guided to flow through the coupler 105 and the gas-delivering circuit 103, and finally to the patient for medical treatment. In a possible implementation, the gas-delivering circuit 103 may include a nasal canal, a tracheostomy tube, or a respiratory mask, etc.

Figure 2:
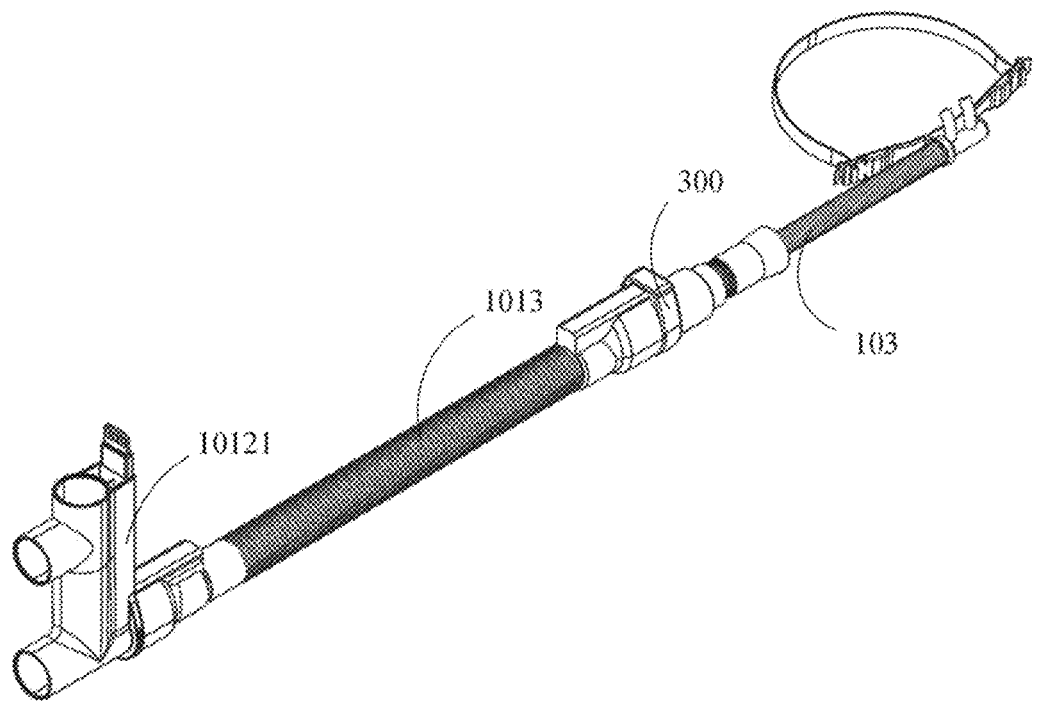
FIG. 2 shows a schematic structural diagram of a respiratory system provided by an embodiment of the present application

FIG. 2 shows a schematic structural diagram of a respiratory system provided by an embodiment of the present application. In a possible implementation, the gas-providing circuit may further include a respiratory conduit 1013, and the chamber adaptor 10121, the respiratory conduit 1013, the coupler 102 and the gas-delivering circuit 103 are connected in a row in a sealed manner to prevent gas leakage. The oxygen and compressed air are provided into the circuit through an inlet of the chamber adaptor 10121, and are finally provided to the patient through an outlet of the gas-delivering circuit 103.

As shown in FIG. 3A-FIG. 3C, an embodiment of the present application provides a coupler 300, including: a first connecting portion 301, an accommodating portion 302 and a second connecting portion 303, where:

the first connecting portion 301 is operatively connected to a gas-providing circuit;

the second connecting portion 303 is operatively connected to a gas-delivering circuit, where the gas-providing circuit, the coupler 300 and the gas-delivering circuit form a pathway for providing gas to a user at a patient side of the coupler 300;

the accommodating portion 302 is provided with at least one sensing apparatus, where the at least one sensing apparatus is configured to measure a first parameter of the gas passing through the coupler 300.

With reference to FIG. 1, FIG. 2 and FIG. 3A-FIG. 3C, the first connecting portion 301 is connected to the gas-providing circuit 101, as described above, the gas-providing circuit 101 may include a main board device 1011, a gas-heating conduit 1012 and a respiratory conduit 1013. The gas provided by the gas-providing circuit 101 is delivered to the coupler 300 for further processing. The gas-heating conduit 1012 is operatively connected to the main board device 1011 and the first connecting portion 301 of the coupler 300 respectively.

In a possible implementation, the coupler 300 may be triggered to operate upon receiving a triggering instruction from the main board device 1011. In another possible implementation, the coupler 300 may be triggered to operate under a condition that the first connecting portion 301 and the second connecting portion 303 are respectively assembled to the gas-providing circuit 101 and the gas-delivering circuit 103.

Referring to FIG. 4, the accommodating portion 302 is provided with at least one sensing apparatus 3021, which may be connected in a detachable manner or an embedded manner. In a possible implementation, the sensing apparatus 3021 may be any one or more of the following sensing apparatuses: an FiO2 sensor, an SpO2 sensor, a humidity sensor, a sensor for detecting a breath rate, a sensor for detecting an ambient temperature, and a sensor for detecting a temperature of the gas (such as a negative temperature coefficient (NTC) sensor). The one or more sensing apparatuses 3021 may be evenly distributed along inner or outer circumferential surface of the accommodating portion 302, for example, in an embedded manner, or may be located at one protrusion of the accommodating portion 302 as shown in FIG. 3A-FIG. 3C. Further, the one or more sensing apparatuses 3021 are configured to measure first parameters corresponding to each of the sensing apparatuses 3021. The coupler 300 may further include a heating apparatus 3022 operatively connected to the accommodating portion 302 in a detachable manner or an embedded manner. The heating apparatus 3022 is configured to heat the gas passing through the coupler 300 delivered by the gas-providing circuit 101. In a possible implementation, the gas may have already been heated in previous components (such as in the chamber 10122 or through wires arranged between the main control board 1011 and the coupler 300) of the respiratory system 100, and in such case the heating apparatus 3022 is configured to preserve the temperature of the heated gas, since a relatively long routine has the gas travelled before it arrives in the coupler 300, and the temperature may be reduced due to, for example, cooling down by an inner wall of the respiratory conduit 1013.

In a possible implementation, the sensing apparatus 3021 may be configured to send the first parameter of the gas to the main board device 1011.

The sensing apparatus 3021 may include a passive sensor or an active sensor, and when the sensing apparatus 3021 includes a passive sensor (e.g., a resistance 3027), the sensing apparatus 3021 starts to detect and feed the first parameter back to the main board device 1011 once the coupler 300 is connected into the respiratory system 100 and is powered up; and when the sensing apparatus 3021 includes an active sensor, the sensing apparatus 3021 may start to detect and feedback the first parameter when a triggering instruction is sent to the sensing apparatus 3021 by the main board device 1011.

In a possible implementation, the coupler 300 is powered by the main board device 1011; and in another possible implementation, the coupler 300 further includes a battery 3028 for providing power for the coupler 300.

Illustratively, the coupler 300 may be powered up by the main board device 1011 once the coupler 300 is connected into the respiratory system 100 through wires, so that the coupler 300 could operate normally to implement respective functions thereof. In addition, the coupler 300 may be further provided with a battery 3028 as an auxiliary power, to avoid a case that the main board device 1011 cannot normally provide power to the coupler 300 due to some errors or mistakes. In another implementation, the coupler 300 is not physically connected to the main board device 1011 with wires, but is communicatively connected to the main board device 1011 wirelessly, and in such case, the coupler 300 may be powered up simply by the battery 3028 provided in the coupler 300, and may start to operate upon receiving a triggering instruction from the main board device 1011.

In a possible implementation, a working mode of the coupler 300 is acquired by the main board device 101 according to attribute information provided by the coupler 300.

For example, one coupler 300 may support one or more working modes, and attribute information representing each working mode may be preset in the coupler 300. When the coupler 300 is connected in the respiratory system 100, the main board device 1011 may read the attribute information preset in the coupler 300 (such attribute information may be, for example, preset in a microcontroller unit of the coupler 300), so as to determine whether the working mode of the coupler 300 matches with a coupling mode set in the main board device 1011. When the working mode of the coupler 300 matches with the coupling mode set in the main board device 1011, the respiratory system 100 may operate normally; and when the working mode of the coupler 300 does not match with the coupling mode set in the main board device 1011, at least one of the following manners are implemented:

(1) the main board device 1011 may automatically adjust the coupling mode to a coupling mode that is consistent with the working mode read from the coupler 300, so as to enable the respiratory system 100 to operate normally;

(2) the main board device 1011 may generate a notification to notify the user the inconsistency between the coupling mode and the working mode, so that the user could manually adjust the coupling mode of the main board device 1011 or the coupler 300 to enable the respiratory system 100 to operate normally. It shall be noted that the notification may also be generated, under trigger of the main board device 1011, by a notifying apparatus 3026 provided in the accommodating portion 302 of the coupler 300.

In a possible implementation, the notifying apparatus 3026 may be an audio speaker or a light emitting diode (LED) provided in the accommodating portion 302.

In a possible implementation, the attribute information may be a value of a resistance 3027 provided in the accommodating portion 302 of the coupler 300, and different values of the resistance 3027 correspond to different working modes of the coupler 300.

In a possible implementation, the different working modes of the coupler 300 correspond to different flow rates of the gas. As a possible design, the coupler 300 may be designed to have different diameters for accommodating different flow rates.

Illustratively, the working modes of the coupler 300 may include an adult mode and a pediatric mode, where the adult mode may correspond to a first flow rate, e.g., ranging from 10 to 80 LPM (Liters Per Minute), and the pediatric mode may correspond to a second flow rate, e.g., ranging from 2 to 25 LPM, and the first flow rate is higher than the second flow rate. That is, the main board device 101 will provide gas in a higher flow rate when working under a coupling mode corresponding to the adult mode than that of the pediatric mode, since an excessive flow rate may be harmful for a child, and a low flow rate may not be sufficient for adult treatment. For other examples, different working modes may also be based on different sensor capabilities, e.g. humidification or ambient temperature, or patient demographics, e.g. breath rate, heart rate, pulse oximetry, etc.

In a possible implementation, the coupler 300 further includes at least one of an HEPA (high efficiency particulate air) filter 3023 or a single direction valve 3024 provided in the accommodating portion 302.

Illustratively, an HEPA filter 3023 (as shown in FIG. 4) may be provided on the accommodating portion 302 to filter particulates with certain diameter from the compressed air delivered to the patient, so as to implement respiratory assistance to the patient in a more effective way. In addition, a single direction valve 3024 (as shown in FIG. 4) may also be provided in the accommodating portion 302. The single direction valve 3024 only allows the compressed air to flow toward a patient direction, and avoids exhaled air from the patient to flow back into the respiratory system 100, thereby preventing the conduits and pathways of the respiratory system 100 from being damaged by the exhaled air, and extending serving life of the respiratory system 100. In a possible design, the HEPA filter 3023 and the single direction valve 3024 may be provided at the center of the coupler 300.

In a possible implementation, the coupler 300 may include a user port 3025 provided in the accommodating portion 302, where the user port 3025 is configured to collect physiological information of the user.

Illustratively, the user port 3025 (as shown in FIG. 4) may start to collect physiological information of the patient when the patient taps the user port 3025 by using a finger with a certain pressure, where the physiological information includes, but is not limited to, heart rate, pulse, blood oxygen, blood pressure, vascular sclerosis, heart rate variability (HRV), etc.

Multiple sensors can be embedded within this smart sensor coupler to allow for measurement, heating, detecting, and even notification (audio speaker/colored LEDs). These sensor(s) can be utilized to measure any variable within the gas pathway, and even environments outside the gas pathway, not limited to FiO2, SpO2, gas temperature, humidity, breath rate, ambient temperature, etc. Smart sensor coupler shall allow attachment to a patient interface such as a nasal cannula, tracheostomy tube, respiratory mask, etc. via a standard ISO 5367 connection, and potentially other special adaptations. Smart sensor shall also attach to breathing circuit hose to make a sealed connection, with provisions for at least 1 wire connection, typically 2 or more. Wire connectivity shall be through terminated ends by way of plug, pins, magnetic locking, or proprietary connection interface. Smart sensor coupler may also communicate (wirelessly or by wire) with device, and/or patient interface via app or dedicated remote/patient interface for real time data, feedback algorithms adjustment, patient interface adjustments, etc. Smart coupler can also have a patient port for sampling (e.g. pressure tap). Smart coupler can also have the means to be self-powered (solar, battery, or self-generated) to maintain functionality in the event that device power is disconnected or lost. Pin configuration of smart coupler can be used to identify sensor capabilities, patient modes (pediatric versus adult), or patient demographics.

It should be understood by a person skilled in the art that, the term such as "and/or" in the embodiments of the present application is merely used to describe an association between associated objects, which indicates that there may be three relationships, for example, A and/or B may indicate presence of A only, of both A and B, and of B only.

The term "a" or "an" is not intended to specify one or a single element, instead, it may be used to represent a plurality of elements where appropriate.

In the embodiments of the present application, expressions such as "exemplary" or "for example" are used to indicate illustration of an example or an instance. In the embodiments of the present application, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

Finally, it should be noted that the foregoing embodiments are merely intended for describing the technical solutions of the present application other than limiting the present application. Although the present application is described in detail with reference to the foregoing embodiments, a person of ordinary skill in the art should understand that he may still make modifications to the technical solutions described in the foregoing embodiments, or make equivalent replacements to some technical features thereof, without departing from the spirit and scope of the technical solutions of the embodiments of the present application.

What is claimed is:

1. A respiratory system, comprising:
 a gas-providing circuit;
 a coupler; and
 a gas-delivering circuit;
 wherein the coupler comprises:
 a first connecting portion;
 an accommodating portion; and
 a second connecting portion;
 wherein the first connecting portion is connected to the gas-providing circuit, wherein the gas-providing circuit comprises a gas-heating conduit, and gas passing through the gas-providing circuit to the coupler is heated by the gas-heating conduit, the second connecting portion is connected to the gas-delivering circuit; the gas-providing circuit, the coupler, and the gas-delivering circuit form a pathway for providing the gas to a user at a patient side of the coupler; the accommodating portion is provided with at least one sensor, wherein the at least one sensor is comprises a sensor configured to measure a first parameter of the gas passing through the coupler, and the coupler further comprises a heater configured to heat the gas passing through the coupler;
 wherein the gas-providing circuit further comprises:
 a main board device configured to provide the gas, wherein the coupler is communicatively connected to the main board device and the at least one sensor is configured to send the first parameter of the gas to the main board device;

wherein the coupler is powered by the main board device;
wherein the gas-delivering circuit comprises a conduit and one of a nasal cannula, a tracheostomy tube, or a respiratory mask connected to the conduit;
wherein the system further comprises:
a user port provided in the accommodating portion, wherein the used port is configured to collect physiological information of the user.

2. The system according to claim 1, wherein a working mode of the coupler is acquired by the main board device according to attribute information provided by the coupler.

3. The system according to claim 2, further comprising
a resistance provided in the accommodating portion; wherein the attribute information is a value of the resistance, and different values of the resistance correspond to different working modes of the coupler.

4. The system according to claim 3, wherein the different working modes of the coupler correspond to different flow rates of the gas.

5. The system according to claim 3, wherein the working modes of the coupler comprise an adult mode and a pediatric mode.

6. The system according to claim 5, wherein the adult mode corresponding to a first flow rate of the gas ranging from 10 to 80 LPM, and the pediatric mode corresponding to a second flow rate of the gas ranging from 2 to 25 LPM.

7. The system according to claim 2, wherein the working mode of the coupler is used by the main board device to adjust a coupling mode set on the main board device.

8. The system according to claim 2, further comprising:
an indicator provided in the accommodating portion, wherein the indicator is triggered to generate a notification under a condition that the working mode of the coupler is inconsistent with a coupling mode set on the main board device.

9. The system according to claim 8, wherein the indicator is an audio speaker or a light emitting diode provided in the accommodating portion.

10. The system according to claim 1, wherein the coupler is triggered to operate upon receiving a triggering instruction from the main board device.

11. The system according to claim 1, wherein the gas-heating conduit is operatively connected to the main board device.

12. The system according to claim 1, wherein the coupler is triggered to operate under a condition that the first connecting portion and the second connecting portion are respectively assembled to the gas-providing circuit and the gas-delivering circuit.

13. The system according to claim 1, further comprising a battery for providing power for the coupler.

14. The system according to claim 1, further comprising at least one of an HEPA filter or a single direction valve provided in the accommodating portion.

15. The system according to claim 1, wherein the coupler is operatively connected to the gas-providing circuit in a sealed manner.

16. The system according to claim 1, wherein the at least one sensor comprises at least one of an FiO2 sensor, an SpO2 sensor, a humidity sensor, a sensor configured to detect a breath rate, a sensor configured to detect an ambient temperature, or a sensor configured to detect a temperature of the gas.

17. The system according to claim 1, wherein the at least one sensor or the heater is operatively connected to the accommodating portion in a detachable manner.

* * * * *